United States Patent
Flament et al.

[11] Patent Number: 6,063,041
[45] Date of Patent: May 16, 2000

[54] DEVICE FOR SAMPLING VOLATILE PRODUCTS

[75] Inventors: Ivon Flament, Geneva, Switzerland; Christine Vuilleumier, Collonges-sous-Saleve; Laurence Aymard, St-Julien-en-Genevois, both of France

[73] Assignee: Firmenich SA, Geneva, Switzerland

[21] Appl. No.: 09/117,396

[22] PCT Filed: Nov. 26, 1997

[86] PCT No.: PCT/IB97/01477

§ 371 Date: Jul. 29, 1998

§ 102(e) Date: Jul. 29, 1998

[87] PCT Pub. No.: WO98/28620

PCT Pub. Date: Jul. 2, 1998

[30] Foreign Application Priority Data

Dec. 20, 1996 [CH] Switzerland ............... 3151/96

[51] Int. Cl.$^7$ .................................................. A61B 5/00
[52] U.S. Cl. ............................................................ 600/573
[58] Field of Search ................................... 600/573, 362

[56] References Cited

U.S. PATENT DOCUMENTS

| | | | |
|---|---|---|---|
| 4,190,060 | 2/1980 | Greenleaf et al. | 128/760 |
| 4,398,543 | 8/1983 | Sandlin et al. | 128/760 |
| 4,678,571 | 7/1987 | Hosaka et al. | 210/202 |
| 4,909,256 | 3/1990 | Peck | 128/632 |
| 5,301,685 | 4/1994 | Guirguis | 600/573 |

FOREIGN PATENT DOCUMENTS

Wo 89/04630  6/1989  WIPO .

OTHER PUBLICATIONS

C. Vuilleumier et al., "Headspace Measurement of Evaporation Rates of Perfumes Applied onto Skin: Application to Rose Essential Oils and Their Principal Components", *Perfumer & Flavorist*, vol. 20, pp. 1–9 (Mar./Apr. 1995).

A. Baydar et al., "Skin Odor Value Technology for Fragrance Performance Optimization", *Perfumer & Flavorist*, vol. 20, pp. 45–53 (Sep./Oct. 1995).

*Primary Examiner*—Max Hindenburg
*Assistant Examiner*—Pamela Wingood
*Attorney, Agent, or Firm*—Pennie & Edmonds LLP

[57] ABSTRACT

The present invention concerns a device for collecting volatile products deposited on a surface, which comprises a housing having an open end and defining an internal cavity which runs into said opening, said housing containing a material for adsorbing said volatile compounds. The opening can be sealed by means of a stopper and is closed in the out-of-use position and adapted to be in contact with said surface in the operation position. The device is particularly appropriate for capturing volatile compounds from a perfuming composition which has been applied onto the skin.

12 Claims, 3 Drawing Sheets

DEVICE FOR SAMPLING VOLATILE PRODUCTS

TECHNICAL FIELD AND PRIOR ART

The present invention concerns a device for collecting volatile products deposited on a surface in static mode, as well as a kit or package comprising such a collecting device and a support for the sampling of the headspace volatiles emitted by a perfuming composition applied onto the skin.

It is known in the perfume industry, that the measurement of the diffusion of volatile compounds from the skin or hair, or also from other types of perfumed surfaces, is essential for assessing the olfactive performance of perfuming compositions, in the form of perfumes, colognes, or in cosmetics such as creams, shampoos, soaps, etc. This measurement can be carried out in vivo in order to study the diffusion profile of said perfuming compositions applied onto different skin types and comprises, in general, two distinct stages, i.e. the collection of the headspace, then the analysis of the volatile compounds captured, each of the stages having its own limits.

With respect to the first stage, the so-called "Headspace" analysis techniques can be used, which are based on the trapping of the compounds of the gaseous phase in the direct environment of the surface zone of the body studied, for example by adsorption on a solid porous material; the thus trapped components are then desorbed, generally thermally, and analyzed by chromatography, spectrometry or any other appropriate method.

Dynamic sampling of volatiles has been considered up until now as being more efficient, since it makes it possible to enrich the adsorbing material in volatile, or even semi-volatile, products. Equipments intended for the dynamic collection of perfume headspace are described, for example, by Vuilleumier et al. in Perfumer & Flavorist, vol. 20, p. 1–9, March/April 1995, and by Baydar et al., in the same journal, vol. 20, p. 45–53, September/October. 1995.

However, the apparatuses described in the above publications have the disadvantage of requiring the use of a calibrated pump, in order to precisely know the gaseous volume pumped in the course of the capturing process, and the presence of a filter, for example an activated charcoal-based filter, to avoid the contamination of the air circulating inside the system. Moreover, these equipments are bulky, as they require, for example, that a hermetically sealed sleeve is applied around a body member (for example, an arm), as well as operation by a specialist, and that they are not easy to transport and cannot be used without an energy source.

The object of the present invention is to overcome the drawbacks of the known headspace analysis devices, by providing a device which is easy to use, even by non-specialists, inexpensive and can be carried, while assuring a reliable and reproducible sampling of the volatile products.

DESCRIPTION OF THE INVENTION

The miniature device for sampling or collecting volatile compounds deposited on a surface which is the object of the present invention is characterized in that it comprises a housing having an open end and defining an internal cavity which runs into the said opening and which contains a material capable of adsorbing said volatile compounds, and in that said opening can be closed by means of a stopper, is closed when in the out-of-use position and is adapted to be in contact with said surface when in the operation position.

More particularly, and according to a possible embodiment of the invention, the housing is formed of two parts which can be fitted into each other, such as to retain in-between the adsorbing material, the latter being retained by a microgrid which is preferably made of an inert material such as for example Teflon®, stainless steel, etc. The collecting device further comprises a third part which forms, in the out-of-use-position, a stopper which hermetically seals the opening of said housing. Preferably, the three parts which form the device are of cylindrical shape and made of a hard and essentially inert plastic material, for example polycarbonate, polypropylene, Teflon®, etc.

According to a variant of the invention, the adsorbing product is maintained as a powder between a microgrid, as mentioned beforehand, and a filter made of, for example, cellulose, glass fiber, Teflon®, etc.

With respect to the material which can be used as the powder in the collecting device of the invention, its choice is dependent, on the one hand, on the nature of the volatile compounds to be collected and, on the other hand, on the type of analysis to be run. In practice, one can mention, as non-limiting examples, silica gel, carbon black, activated charcoal, Porapak®, Tenax®, Chromosorb ®, etc.

On the other hand, the adsorbing material can also be in a form other than a powder, for example in the form of a foam, graft polymer, other solid porous material, etc; in this case, the microgrid and the filter mentioned beforehand might then be superfluous, the adsorbing material being held as such inside the housing.

Finally, another object of the present invention is a portable collecting system for perfuming compositions applied onto the skin, comprising a collecting device as described above, as well as a support designed to keep the latter in contact with a part of the body of an individual and provided with means to fasten it to this body part. Such a system thus allows non-specialists to easily carry out the collecting process in situ; subsequently, and these steps can also be carried out by a non-specialist, the devices of the present invention can be sealed hermetically, stocked and transported to an appropriate laboratory, where they will then be given to specialists for the analysis of the collected volatile compounds.

BRIEF DESCRIPTION OF THE DRAWINGS

The present invention will now be illustrated in greater detail by reference to a particular embodiment and to the annexed drawings.

DETAILED DESCRIPTION OF THE INVENTION

Figure 1:
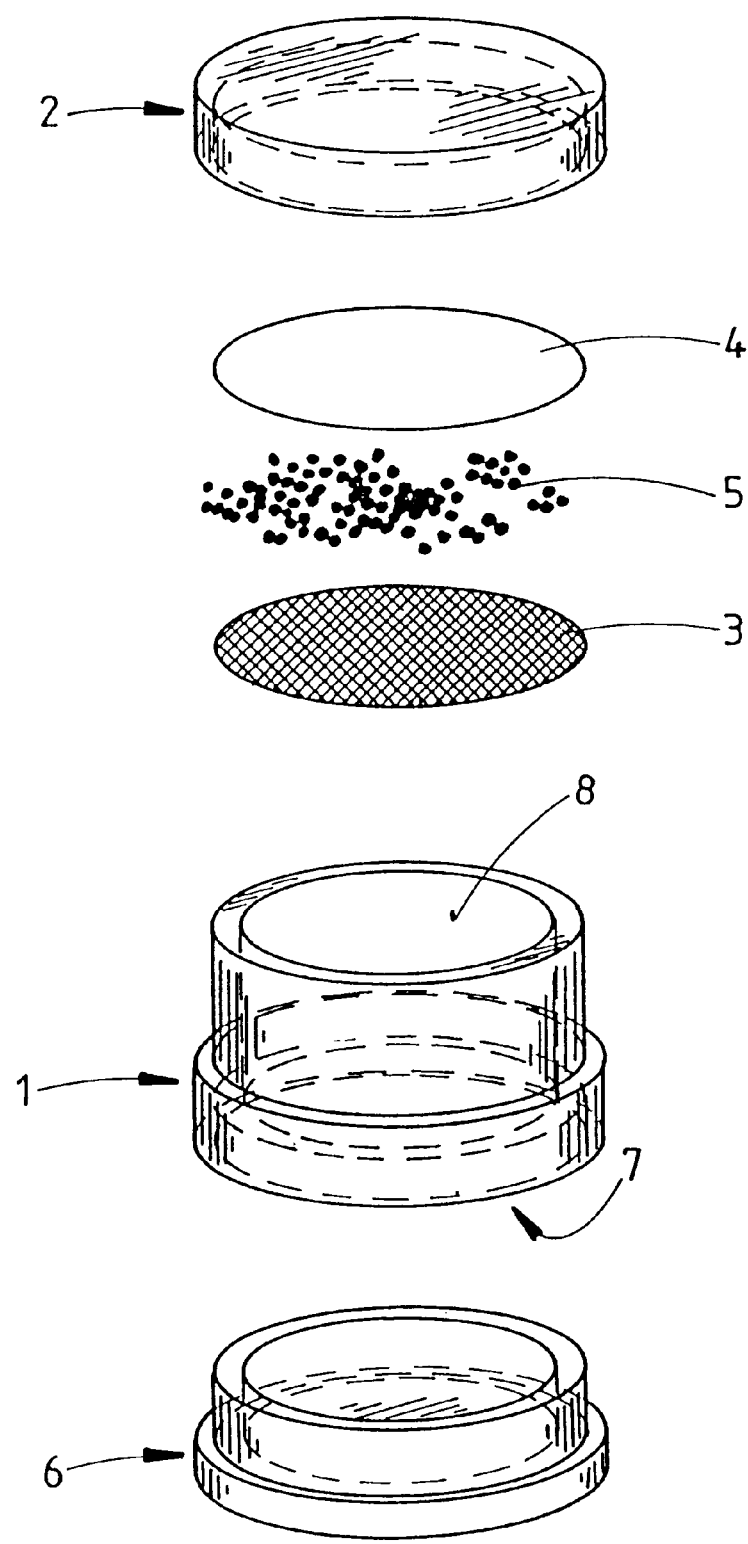
FIG. 1 illustrates a split view of an embodiment of the collecting device.
Figure 2:
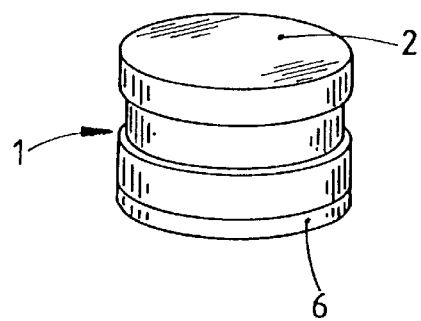
FIG. 2 illustrates a view of an embodiment of the collecting device in the closed out-of-use-position.

Referring first to FIGS. 1 and 2, the collecting device of the invention as illustrated is formed of three cylindrical parts, for example of a transparent polycarbonate, and which can be fitted into each other; more particularly, the device is composed of a central part 1 in form of a sleeve having an axial opening, for example of a diameter of about 25 mm, a recessed upper part 2 which can be fitted into said central part 1 so as to close the upper opening of the latter and maintain, wedged in-between these two parts, the assembly comprising a microgrid 3, which may be formed of, for example, stainless steel, a filter 4, which may be formed of, for example, cellulose, and an adsorbing material 5 which may be formed of, for example, Tenax® (100 mg; 35–60 mesh) and which is placed between the microgrid 3 and the filter 4. Finally, a third recessed part 6 which can be fitted into the lower opening 7 of the central part 1 serves as a stopper to hermetically seal the cavity 8 defined by the central part 1, and which, in the illustrated embodiment, has a volume of the order of 6–7 ml (between the microgrid 3 and the opening 7).

When one wishes to collect volatile compounds on a surface (such as, for example, a textile, a synthetic lining, wood, etc), one just has to remove the lower part 6 which serves as a stopper and apply the device onto the said surface, while maintaining the lower opening 7 in the best possible hermetical contact with the latter. The volatile compounds present on this surface will then diffuse into the evaporation cavity 8 and through the microgrid 3 to reach the adsorbant material 5. Once the collecting of the volatiles has been finished, for a period of time which is determined as a function of the nature of the compounds to be analyzed (5 to 20 minutes, for example), the stopper 6 is put back into its place to hermetically seal the cavity 8. The thus stoppered collecting device (FIG. 2) can be kept without loss of the trapped volatile products, until the analysis of these products is carried out. The adsorbing powder containing the said volatile products is then transferred into a tube and subsequently thermally desorbed for analysis of the captured products, for example by chromatography.

Figure 3:
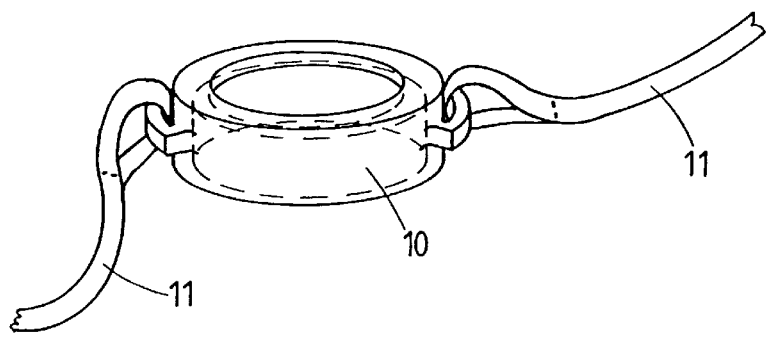
FIG. 3 illustrates a view of an embodiment of the support for the collecting device.

In case of the particular use of the collecting device of the invention for the study of the diffusion of perfuming compositions deposited on the skin of an individual, a support element as illustrated for example in FIG. 3 can be used, which element consists of a cylindrical capsule 10, the inner diameter of which is adapted to the external diameter of the collecting device, as illustrated in FIG. 2, and in such a way as to function as a housing for the latter. The capsule 10 is further provided with fastening means, for example in the form of two strips 11, at least one portion of which has means for attaching the strips to each other, for example of the Velcro® type.

Figure 4:
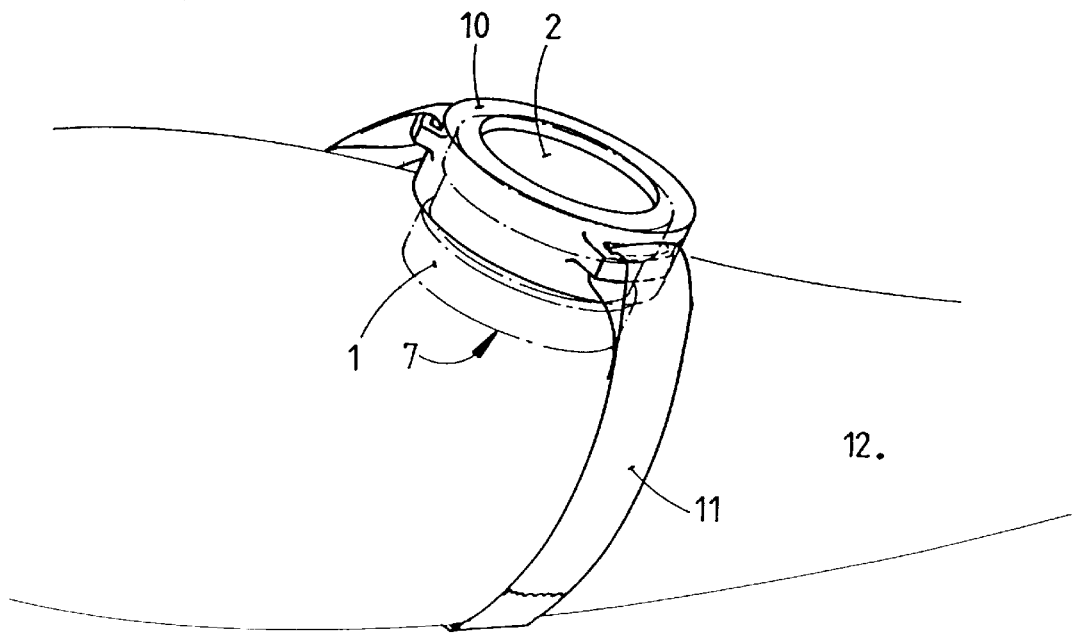
FIG. 4 illustrates a view of a sampling device formed of the collecting device and the support, positioned for use on the forearm of an individual.

As illustrated in FIG. 4, there can thus be realized a sampling device which is formed of the collecting device, the stopper 6 of which has been removed and the lower opening 7 of which is put into contact which the skin of an individual (here, for example, of a forearm 12), and of the support 10, with the fastening strips 11 being fastened around the body part upon which the sampling is carried out.

By means of such device, the diffusion of four volatile chemical compounds contained in a cologne, namely 0.3% cyclamen aldehyde [3-(4-isopropylphenyl)-2-methyl-propanal; origin: Firmenich SA, Geneva, Switzerland], 2.9% of α-isomethylionone, 1.3% of Hedione® (methyl dihydrojasmonate, product of Firmenich SA, Geneva) and 0.7% of muscone, has been studied.

To this end, 10 microliters of the perfuming composition were applied on the two forearms of a female panelist of the Caucasian race, and four collection runs of 15 minutes each were carried out simultaneously on the two arms, directly after applying the composition, and then after respectively 1, 3 and 5 hours. Between collection runs, the sampling device was removed, thus leaving the arm exposed to air.

Figures 5A, 5B:
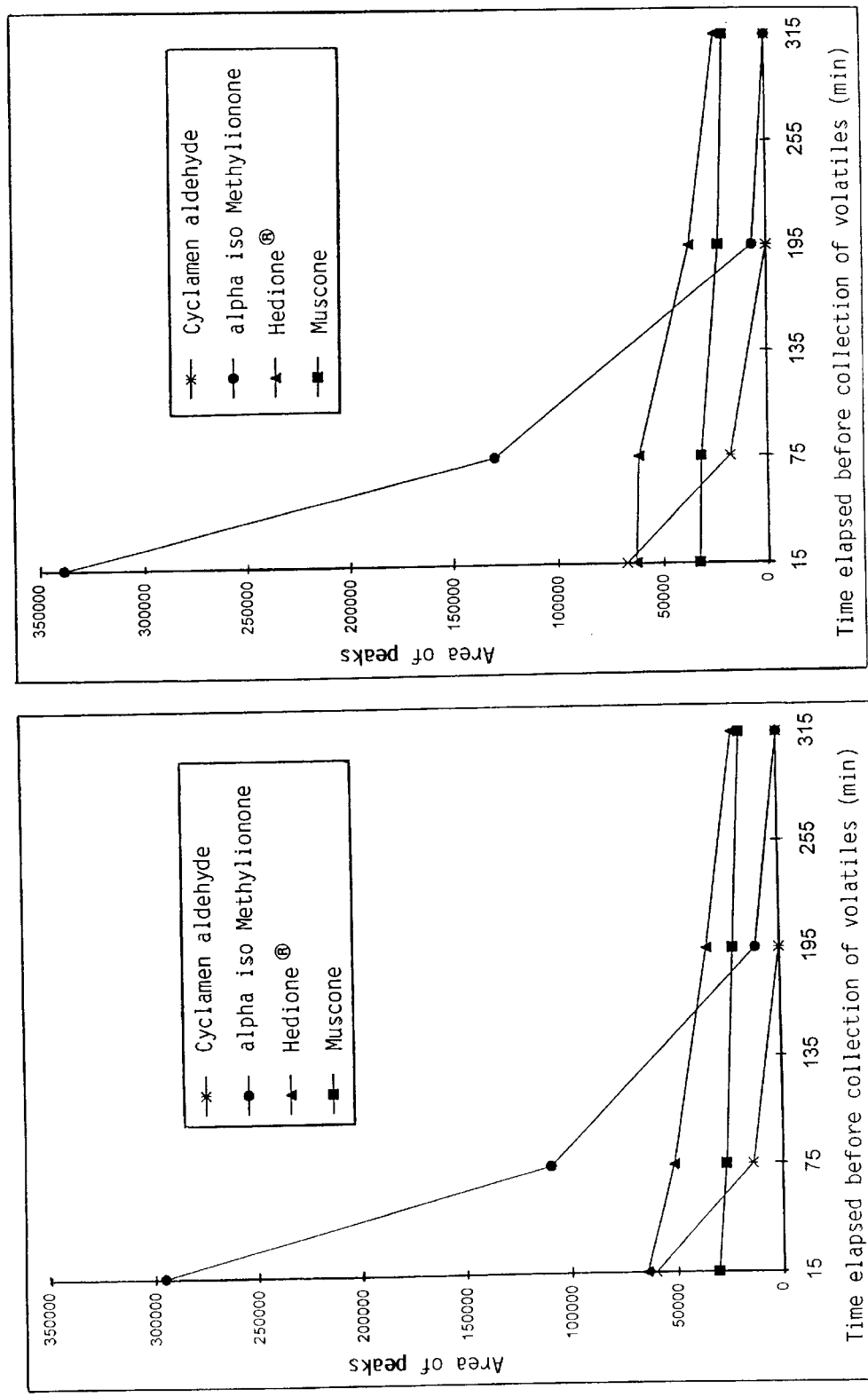
FIGS. 5a and 5b are graphical drawings representing the diffusion profiles obtained for four components of a cologne applied onto the two forearms of a person, which profiles were obtained with the sampling device according to the invention, after collection, desorption and analysis of the collected volatile products.

After thermal desorption, the four volatile compounds were analyzed by combined chromatography/mass spectrometry, and the results obtained were reported on the graphs of FIGS. 5a and 5b.

More particularly, the adsorbing powder containing the volatile products to be analyzed was transferred into a cartridge, and said products thermally desorbed at about 220° C., then condensed into a trap at about −30° C., and again heated to about 220° C., then injected into the chromatograph. In practice, there was used here a combined apparatus comprising an automatic thermal desorption system of the type Perkin Elmer AID 400, as well as a coupled apparatus formed of a chromatograph of the type Hewlett Packard 6890 Series GC System (with an apolar column having a length of 30 m, an internal diameter of 0.32 mm and a phase thickness of 1.0 $\mu$m) and of a mass spectrometer of the type Hewlett Packard 6890 Series Mass Selective Detector.

The observed results show a good reproducibility of the tests carried out on the two arms. All evaporation kinetics of the products diminish in the course of the time, but their profiles are well differentiated. Thus, the decrease is pronounced and fast for cyclamen aldehyde and α-iso methylionone, and more moderate for Hedione®; on the other hand, it is very weak for muscone. At the beginning of the collection runs, a strong contribution of the more volatile products can be observed, to the detriment of the less volatile, but after about 5 hours, the inverse phenomenon is observed. This observation confirms well the results obtained by a "dynamic Headspace" analysis, and the fact that in alcoholic applications the behavior of a perfume is essentially determined by the volatility of the different compounds forming the perfume.

The collecting device of the invention thus makes it possible to carry out a statical measurement over a short period of time of volatile compounds which diffuse from a given surface, in a simple manner and, in what concerns the collecting process itself, which can be carried out in situ, accessible to non-specialists.

The device of the present invention is very simple in conception and in its realization; it can be easily transported, and calibrations can be carried out. Furthermore, thanks to the miniature size of the device, it can be easily used, by means of an appropriate supporting element, on different parts of the body, in order to test the behavior of a perfumed composition on the latter, the step of collecting the volatile compounds being easily carried out in situ by non-specialists. Finally, due to their simplicity, these devices are inexpensive and can hence be considered as disposable.

What is claimed is:

1. Device for collecting volatile products applied onto a surface, comprising a housing having an open end and defining an internal cavity which runs into said open end, which housing has an operation position and an out-of-use position and contains a material for adsorbing said volatile compounds, wherein said open end can be closed by a stopper, and wherein the housing is closed when in the out-of-use position and adapted to be in contact with said surface when in the operation position.

2. Device according to claim 1, wherein the housing is formed of two parts which can be fitted into each other, such that said adsorbing material, in the form of a powder and retained by a microgrid, is kept in-between said two parts.

3. Device according to claim 2, wherein the adsorbing material is lodged between a microgrid and a filter, said microgrid and said filter being composed of an inert material.

4. Device according to claim 2, wherein the two parts forming the housing are cylindrical and formed of a hard and substantially inert material.

5. Device according to claim 1, wherein the adsorbing material is a foam, a graft polymer or a porous solid material.

6. Device for collecting volatile products from a perfuming composition applied onto the skin of an individual, according to claim 1, wherein said device further comprises a support designed to maintain said collecting device in contact with a part of the body of said individual and means for fastening the device to said part of the body.

7. Device according to claim 6, wherein the support consists of a capsule having a housing intended for receiving the collecting device and equipped with two fastening strips provided with means for attaching said strips to each other.

8. Device for collecting volatile products applied onto a surface, comprising a housing having open and closed ends and defining an internal cavity which runs into said open end, and a stopper, which housing has an operation position and an out-of-use position and contains a material for adsorbing said volatile compounds, wherein said open end is closed by the stopper when the housing is in the out-of-use position and said open end is open and in contact with said surface when the housing is in the operation position.

9. Device according to claim 8, wherein the housing is formed of two parts which are configured and dimensioned to fit together, the absorbing material is in the form of a powder, and the absorbing material is retained in the housing by a microgrid which is held between the two parts of the housing when the parts are fit together.

10. Device according to claim 9, wherein the two parts forming the housing and the stopper which seals the open end of said housing in the out-of-use position are cylindrical and formed of a hard and substantially inert material.

11. Device according to claim 9, wherein the adsorbing material is lodged between the microgrid and a filter made of an inert material.

12. Device according to claim 8, wherein the adsorbing material is a foam, a graft polyol or a porous solid material.

* * * * *